United States Patent
Kim et al.

(10) Patent No.: US 9,535,134 B2
(45) Date of Patent: Jan. 3, 2017

(54) METHOD FOR DIAGNOSING INTERNAL FAULT OF OIL-IMMERSED TRANSFORMER THROUGH CONTENT RATIOS OF DISSOLVED GASES

(71) Applicant: HYOSUNG CORPORATION, Seoul (KR)

(72) Inventors: Young-Min Kim, Changwon-si (KR); Sung-Jik Kim, Gimhae-si (KR); Hwang-Dong Seo, Gimhae-si (KR); Soo-Jin Lee, Changwon-si (KR)

(73) Assignee: HYOSUNG CORPORATION, Seoul (KR)

( * ) Notice: Subject to any disclaimer, the term of this patent is extended or adjusted under 35 U.S.C. 154(b) by 224 days.

(21) Appl. No.: 14/368,476

(22) PCT Filed: Dec. 26, 2012

(86) PCT No.: PCT/KR2012/011506
§ 371 (c)(1),
(2) Date: Jun. 24, 2014

(87) PCT Pub. No.: WO2013/100593
PCT Pub. Date: Jul. 4, 2013

(65) Prior Publication Data
US 2015/0007635 A1 Jan. 8, 2015

(30) Foreign Application Priority Data

Dec. 26, 2011 (KR) .................. 10-2011-0142841
Dec. 26, 2011 (KR) .................. 10-2011-0142843

(51) Int. Cl.
*G01F 25/00* (2006.01)
*G01R 31/40* (2014.01)
(Continued)

(52) U.S. Cl.
CPC .......... *G01R 31/40* (2013.01); *G01N 33/0004* (2013.01); *G01N 33/26* (2013.01);
(Continued)

(58) Field of Classification Search
CPC ...................................................... G01F 25/00
(Continued)

(56) References Cited

U.S. PATENT DOCUMENTS

| | | | |
|---|---|---|---|
| 2012/0290229 A1* | 11/2012 | Cavallini | G01R 31/1281 702/58 |
| 2015/0007635 A1* | 1/2015 | Kim | G01N 33/2841 73/19.1 |
| 2015/0020572 A1* | 1/2015 | Kim | G01R 31/027 73/19.01 |

OTHER PUBLICATIONS

Michel Duval, 'Interpretation of Gas-In-Oil Analysis Using New IEC Publication 60599 and IEC TC 10 Database', DEIS, Mar./Apr. 2001—vol. 17, No. 2.*

(Continued)

*Primary Examiner* — David Gray
*Assistant Examiner* — Kevin Butler
(74) *Attorney, Agent, or Firm* — Novick, Kim & Lee, PLLC; Jae Youn Kim

(57) ABSTRACT

A method for accurately diagnosing an internal fault of an oil-immersed transformer by analyzing content ratios of dissolved gases generated when the internal fault occurs in the oil-immersed transformer is provided. The method diagnoses the internal fault by analyzing the dissolved gases contained in the insulating oil of the oil-immersed transformer for internal fault diagnosis, wherein the method comprises: a first step of extracting H2, CH4, C2H4, and C2H2 from the dissolved gases; a second step of calculating a content ratio (%) of each dissolved gas from the total content of the four dissolved gases selected from the extracted five dissolved gases; and a third step of determin- (Continued)

ing the internal fault of the oil-immersed transformer for diagnosis corresponding to an internal fault region according to content ratio (%) values of the calculated four dissolved gases and predetermined content ratios (%) of the four dissolved gases.

18 Claims, 8 Drawing Sheets

(51) Int. Cl.
    *G01N 33/28*     (2006.01)
    *G01N 33/00*     (2006.01)
    *G01N 33/26*     (2006.01)
    *H01F 27/12*     (2006.01)
    *H01F 27/40*     (2006.01)
    *G01F 1/72*     (2006.01)
    *G01F 1/698*     (2006.01)
    *G01R 31/02*     (2006.01)

(52) U.S. Cl.
    CPC ......... *G01N 33/2841* (2013.01); *H01F 27/12* (2013.01); *H01F 27/402* (2013.01); *G01F 1/698* (2013.01); *G01F 1/72* (2013.01); *G01F 25/0007* (2013.01); *G01F 25/0015* (2013.01); *G01F 25/0053* (2013.01); *G01R 31/027* (2013.01)

(58) Field of Classification Search
    USPC .................................................. 73/19, 19.1
    See application file for complete search history.

(56) References Cited

OTHER PUBLICATIONS

HyoSung Corporation, Written Opinion of the International Searching Authoriity, PCT/KR2012/011504, Apr. 12, 2013.*
HyoSung Corporation, Written Opinion of the International Searching Authoriity, PCT/KR2012/011506, Apr. 29, 2013.*
Jin Yeub Park et al. "A study on failure diagnosis examples of Large oil filled transformer using dissolved gas analysis." The Korean Institute of Electrical Engineers, Journal of 2009 Summer Conference, pp. 740-741 (Jul. 14, 2009).
A. Akbari et al. "A Software Implementation of the Duval Triangle Method." Electrical Insulation, 2008. Conference Record of the 2008 IEEE International Symposium. pp. 124-127 (Jun. 9, 2008).
Sukhbir Singh et al. "Duval Triangle : A Noble Technique for DGA in Power Transformers." International Journal of Electrical and Power Engineering, vol. 4, Issue 3, pp. 193-197 (2010).
Michel Duval. "The Duval Triangle for Load Tap Changers, Non-Mineral Oils and Low Temperature Faults in Transformers" IEEE Electrical Insulation Magazine, vol. 24, No. 6, pp. 22-29 (Nov. 2008).
Michel Duval et al. "Improving the Reliability of Transformer Gas-in Oil Diagnosis." IEEE Electrical Insulation Magazine, Vo. 21, No. 4, pp. 21-27 (Jul. 2005).

* cited by examiner

METHOD FOR DIAGNOSING INTERNAL FAULT OF OIL-IMMERSED TRANSFORMER THROUGH CONTENT RATIOS OF DISSOLVED GASES

TECHNICAL FIELD

The present invention relates to a method of diagnosing an internal fault of an oil-immersed transformer, and more particularly, to a method of accurately diagnosing an internal fault of an oil-immersed transformer by analyzing a content ratio of dissolved gases generated when the internal fault occurs in the oil-immersed transformer.

BACKGROUND ART

An oil-immersed transformer installed in a transformer substation or an electric power plant is one of the more important components of an electric power supplying system, and it is required to have high reliability. The oil-immersed transformer may have its electrical and mechanical performance degraded due to deterioration during operation, which causes an abnormal condition of the oil-immersed transformer. This phenomenon may cause a serious accident if it may not be detected in advance and appropriately treated.

When an abnormal phenomenon such as dielectric breakdown, local overheating, and the like occurs in the oil-immersed transformer, this phenomenon always accompanies a generation of heat. An insulating material, such as insulating oil, an insulating paper, pressboard, and the like contacting a heat-generating source is affected by the heat and dissolved by a chemical reaction to generate gases. Most of these gases are melted in the insulating oil. Therefore, when gases are extracted and analyzed from the insulating oil taken from the oil-immersed transformer, a type and an extent of the fault occurring in the transformer may be diagnosed.

In the method of diagnosing the oil-immersed transformer through an analysis of dissolved gases, complicated procedure and intense efforts are required, but the diagnosis ratio of an internal fault in the oil-immersed transformer is high. Accordingly, this method is widely used worldwide.

The types of the internal faults in the oil-immersed transformer and the method of diagnosing the internal fault of the oil-immersed transformer through the dissolved gases are prescribed in the international standard (IEC 60599: Mineral oil-impregnated electrical equipment in service guide to the interpretation of dissolved and free gases analysis and IEEE C57.104: IEEE Guide for the interpretation of gases in oil-immersed transformer), and most of the electric power companies and users of oil-immersed electric power devices estimate the internal fault depending on the international standard.

The types of faults described in these international standards are classified into an electrical fault and a thermal fault, and more specifically into six faults including partial discharges, discharges of low energy D1, discharges of high energy D2, a first thermal fault (t<300° C.) T1, a second thermal fault (300° C.<t<700° C.) T2, and a third thermal fault (t>700° C.) T3. Further, the gases that are subject to analysis in the international standards include five compounds such as hydrogen H2, methane CH4, ethane C2H2, ethylene C2H4, and acetylene C2H2.

Conventionally, the classification of faults is determined by analyzing a composition ratio of the five gases, a content ratio of each of the five gases, a range of a key gas, and the like. However, in the conventional method of diagnosing the internal fault of the oil-immersed transformer, there are problems as follows:

First, in the diagnosis method using the key gas, since the fault is diagnosed by using only the key gas (a maximum gas value), a pattern, a composition, and a variation according to energy in each fault cannot be applied to the diagnosis method, resulting in an increase in a ratio of wrong diagnosis. For example, if not the key gas but another gas has the maximum value, there is a problem in that a region is present in which the diagnosis is impossible.

On the other hand, in the diagnosis method using the composition ratio of the five gases, since a result of the diagnosis is established as a pattern, the composition, and variation of gas is applied, the accuracy of the diagnosis is higher. However, it is impossible to diagnose the internal fault of the transformer when the internal fault is not one of the above-mentioned types of the faults and not of the ratio of gas in each fault.

Meanwhile, in the diagnosis method using the content ratio of the gas, there is no region in which the diagnosis is impossible, and the accuracy of the diagnosis is higher. However, only three gases having high energy of the fault are used, and the low-energy hydrogen and ethane are not applied to the diagnosis. Accordingly, there is a problem in that it is difficult to diagnose an initial fault.

Therefore, there is required the development of a technology that can diagnose the internal fault of the oil-immersed transformer. In such a technology, the reliability of the diagnosis for the internal fault of the oil-immersed transformer can be improved and all kinds of faults can be diagnosed.

DISCLOSURE OF THE INVENTION

Technical Problems

The present invention has been to solve the above-mentioned problems in the conventional art. An aspect of the present invention is to provide a method of diagnosing an internal fault of a corresponding oil-immersed transformer through a combination of a content ratio of dissolved gases. By using this combination of content ratios of two dissolved gases among the content ratios of four dissolved gases selected from five dissolved gases generated when the internal fault occurs in the oil-immersed transformer, it achieves the objective of accurately diagnosing the internal fault of the corresponding oil-immersed transformer.

Further, another aspect of the present invention is to provide a method of diagnosing an internal fault of an oil-immersed transformer through a content ratio of dissolved gases. By using the content ratios of four dissolved gases selected from five dissolved gases when the internal fault occurs in the oil-immersed transformer, it achieves the objective of accurately diagnosing the internal fault of the corresponding oil-immersed transformer.

Means to Solve the Problem

In accordance with an aspect of the present invention, there is provided a method of diagnosing an internal fault of an oil-immersed transformer through a combination of content ratios of dissolved gases, which is capable of analyzing the dissolved gases contained in the insulation oil of the oil-immersed transformer of which the internal fault is able to be diagnosed. The method includes: a first step of extracting H2, CH4, C2H2, C2H4, and C2H6 from the dissolved gases; a second step of selecting four dissolved gases, classified depending on each internal fault, from the five extracted and dissolved gases, so as to calculate a content ratio of each dissolved gas to a total content of the four selected and dissolved gases; and a third step of determining a type of the internal fault of the immersed transformer for the diagnosis by enabling one to four combinations, which are selected from combinations of % H2 and % CH4, % H2 and % C2H2, % C2H4 and % C2H2, % C2H4 and % CH4, % H2 and % C2H6, and % C2H4 and % C2H6 which are calculated, to correspond to a predetermined internal fault region.

In the embodiment of the present invention, the third step includes: setting values of the content ratio of % H2 and % CH4 of each oil-immersed transformer, of which a type of the internal faults is known, depending on each of a partial discharge PD, a low energy discharge D1, a high energy discharge D2, a first thermal fault (t<300° C.) T1, a second thermal fault (300° C.<t<700° C.), and a third thermal fault (t>700° C.) T3; and classifying half a region of the first xy-plane into a partial discharge (PD) fault region, a low energy discharge (D1) fault region, a high energy discharge (D2) fault region, a first thermal fault (t<300° C.) (T1) region, a second thermal fault (300° C.<t<700° C.) (T2) region, and a thermal fault (t>700° C.) region by using the plurality of set coordinates, wherein the internal fault of the oil-immersed transformer for the diagnosis is determined by using a region corresponding to x and y coordinates for the values of % H2 and % CH4 calculated in the second step.

In the embodiment of the present invention, the third step includes: setting of the values of % H2 and % C2H2, which are content ratios indicated depending on each of a partial discharge (PD), a low energy discharge (D1), and a high energy discharge (D2) of a thermal fault and an electrical fault, as x and y coordinates for each of a plurality of oil-immersed transformers, of which a type of the internal fault is known, on a second xy-plane; and classifying half a region of the second xy-plane into the partial discharge (PD) fault region, a low energy discharge (D1) fault region, and a high energy discharge (D2) fault region of a thermal fault region and an electrical region, wherein the internal fault of the oil-immersed transformer used for diagnosis is determined by using a region corresponding to x and y coordinates for the values of % H2 and % C2H2 calculated in the second step.

In the embodiment of the present invention, the third step includes: setting values of the content ratio of % C2H4 and % C2H2 of each oil-immersed transformer, of which a type of the internal fault is known, depending on each of a partial discharge PD, a low energy discharge D1, a high energy discharge D2, a first thermal fault (t<300° C.) T1, a second thermal fault (300° C.<t<700° C.) T2, and a third thermal fault (t>700° C.) T3, as x and y coordinates on a third xy-plane; and classifying half a region of the first xy-plane into a partial discharge (PD) fault region, a low energy discharge (D1) fault region, a high energy discharge (D2) fault region, a first thermal fault (t<300° C.) (T1) region, a second thermal fault (300° C.<t<700° C.) (T2) region, and a thermal fault (t>700° C.) region by using the plurality of set coordinates, wherein the internal fault of the oil-immersed transformer for the diagnosis is determined by using a region corresponding to x and y coordinates for the values of % C2H4 and % C2H2 calculated in the second step.

In the embodiment of the present invention, the third step includes: setting values of the content ratio of % C2H4 and % CH4 of each oil-immersed transformer, of which a type of the internal faults is known, depending on each of a partial discharge PD, a low energy discharge D1, a high energy discharge D2, a first thermal fault (t<300° C.) T1, a second thermal fault (300° C.<t<700° C.) T2, and a third thermal fault (t>700° C.) T3, as x and y coordinates on a four X-Y plane; and classifying half a region of the fourth xy-plane into a partial discharge (PD) fault region, a low energy discharge (D1) fault region, a high energy discharge (D2) fault region, a first thermal fault (t<300° C.) (T1) region, a second thermal fault (300° C.<t<700° C.) (T2) region, and a thermal fault (t>700° C.) (T3) region by using the plurality of set coordinates, wherein the internal fault of the oil-immersed transformer for the diagnosis is determined by using a region corresponding to x and y coordinates for the values of % C2H4 and % CH4 calculated in the second step.

In the embodiment of the present invention, the values of % H2-% CH4, % H2-% C2H2, % C2H4-% C2H2, and % C2H4-% CH4 are in a range of 0~100% on each x-y axis on the first to fourth xy-plane, and the fault region is located within a triangular shape defined by connecting points, at which the x axis and the y axis are 100%.

In the embodiment of the present invention, the content ratio of each dissolved gas, which is calculated in the second step, is included in the fault region within the triangular shape.

In accordance with the first embodiment of the present invention, there is provided a method of diagnosing an internal fault of an oil-immersed transformer through a combination of content ratios of dissolved gases. The method includes: a first step of extracting the dissolved gases of H2, CH4, C2H2, C2H4, and C2H6 from each oil-immersed transformer of which a type of the internal faults is known; a second step of selecting four dissolved gases, classified depending on each internal fault, from the five extracted and dissolved gases, so as to calculate a content ratio of each dissolved gas to a total content of the four selected and dissolved gases; a third step of classifying half a region of the first xy-plane into the internal fault region by using the plurality of the first x and y coordinates after setting the values of % H2 and % CH4, which are content ratios indicated by each internal fault, as the first x and y coordinates respectively on the first xy-plane; a fourth step of classifying half a region of the second xy-plane into the internal fault region by using the plurality of the second x and y coordinates after setting the values of % H2 and % C2H2, which are content ratios indicated by each internal fault, as the second x and y coordinates respectively on the second xy-plane; a fifth step of classifying half a region of the third xy-plane into the internal fault region by using the plurality of the third x and y coordinates after setting the values of % C2H4 and % C2H2, which are content ratios indicated by each internal fault, as the third x and y coordinates respectively on the third xy-plane; a sixth step of classifying half a region of the fourth xy-plane into the internal fault region by using the plurality of the fourth x and y coordinates after setting the values of % C2H4 and % CH4, which are content ratios indicated by each internal fault, as the fourth x and y coordinates respectively on the fourth xy-plane; a seventh step of calculating the values of % H2, % CH4, % C2H2, and % C2H4, which are content ratios of four dissolved gases extracted from the oil-immersed transformer for the diagnosis after extracting the dissolved gases of H2, CH4, C2H2, and C2H4 from the insulating oil of the oil-immersed transformer for the diagnosis, of which the internal fault is diagnosed; and, an eighth step of determining the internal fault of the oil-immersed transformer for the diagnosis by using one or more values selected from the values of % H2 and % CH4, the values of % H2 and % C2H2, the values of % C2H4 and % C2H2, and the values of % C2H4 and % CH4 among the content ratios of the dissolved gases calculated in the seventh step.

In accordance with the second embodiment of the present invention, there is provided a method of diagnosing an internal fault of an oil-immersed transformer through content ratios of dissolved gases, which is capable of analyzing dissolved gases contained in insulation oil of the oil-immersed transformer of which the internal fault is able to be diagnosed. The method includes: a first step of extracting H2, CH4, C2H4, C2H2, and C2H6 from the dissolved gases; a second step of selecting four dissolved gases, classified depending on each internal fault, from the five extracted dissolved gases, so as to calculate a content ratio of each dissolved gas to a total content of the four selected dissolved gases; and, a third step of determining the internal fault of the oil-immersed gases for the diagnosis in correspondence to the content ratios of the four dissolved gases which are calculated and an internal fault region according to the content ratios of the four dissolved gases which are predetermined.

In the embodiment of the present invention, the second step includes: setting values of the content ratio of % H2, % CH4, % C2H4, and % C2H2 of the dissolved gases of each oil-immersed transformer, of which a type of the internal faults is known, indicated depending on each of a partial discharge PD, a low energy discharge D1, a high energy discharge D2, a first thermal fault (t<300° C.) T1, a second thermal fault (300° C.<t<700° C.), and a third thermal fault (t>700° C.) T3 on a two-dimensional plane in advance; and classifying the two-dimensional plane into six fault regions corresponding to each fault by using the set content ratios, wherein a region corresponding to the four content ratios calculated in the second step is determined in the fault regions divided on the two-dimensional plane, and the internal fault of the oil-immersed transformer for the diagnosis is determined by using the determined fault region.

In the embodiment of the present invention, the two-dimensional plane has a square shape defined by four axes, the values of % H2, % CH4, % C2H4, and % C2H2 are in a range of 0~100% on the four axes respectively, and each of the divided fault regions is located within a diamond shape formed by connecting points, at which the values of % H2, % CH4, % C2H4, and % C2H2 of the four axes are 50% respectively, by straight lines.

In the embodiment of the present invention, among the four axes, the % H2 axis and % C2H4 axis are opposite to each other, and the % C2H2 axis and the % CH4 axis are opposite to each other.

In the embodiment of the present invention, in the two-dimensional plane, one of two values selected from the values of % H2, % CH4, % C2H4, and % C2H2 increases along two axes from each corner defined by the two axes, and the other one decreases.

In the embodiment of the present invention, the four content ratios calculated in the second step are included in the fault region having the diamond shape.

Further, in accordance with the second embodiment of the present invention, there is provided a method of diagnosing an internal fault of an oil-immersed transformer through a composition ratio of dissolved gas. The method includes: a first step of extracting the dissolved gases of H2, CH4, C2H2, C2H4, and C2H6 from each oil-immersed transformer of which a type of the internal fault is known; a second step of selecting four dissolved gases, classified depending on each internal fault, from the five dissolved gases which are extracted from each of a plurality of oil-immersed transformers of which a type of the internal fault is known, so as to calculate a content ratio of each dissolved gas to a total content of the four selected dissolved gases; a third step of setting values of the content ratios of % H2, % CH4, % C2H4, and % C2H2 of the dissolved gases of each oil-immersed transformer, of which a type of the internal faults is known, indicated depending on each of a partial discharge PD, a low energy discharge D1, a high energy discharge D2, a first thermal fault (t<300° C.) T1, a second thermal fault (300° C.<t<700° C.), and a third thermal fault (t>700° C.) T3 on a two-dimensional plane in advance, so as to classify the two-dimensional plane into the fault region corresponding to each fault by using the values of the content ratios which are set; a fourth step of extracting the dissolved gases from insulating oil of the oil-immersed transformer which is able to be diagnosed, so as to calculate the values of % H2, % CH4, % C2H4, and % C2H2, which are the content ratios of the dissolved gases to the total content of the extracted dissolved gases; and, a fifth step of deciding the values of the content ratios of % H2, % CH4, % C2H4, and % C2H2 of the dissolved gases of each oil-immersed transformer for diagnosis, which are calculated in the fourth step in a fault region of the two-dimensional plane, so as to determine the internal fault of the oil-immersed transformer by using the decided fault region.

Advantageous Effects

According to the present invention, the ratio of a wrong diagnosis of the internal fault in the oil-immersed transformer can be reduced.

Further, according to the present invention, since there is no region in which the diagnosis cannot be performed when diagnosing the internal fault of the oil-immersed transformer, the reliability of the diagnosis of the internal fault can be improved.

BEST MODE

Hereinafter, exemplary embodiment of the present invention will be described with reference to the accompanying drawings. In the following description of the present invention, a detailed description of known functions and configurations incorporated herein will be omitted when it may make the subject matter of the present invention rather unclear.

Figure 1:
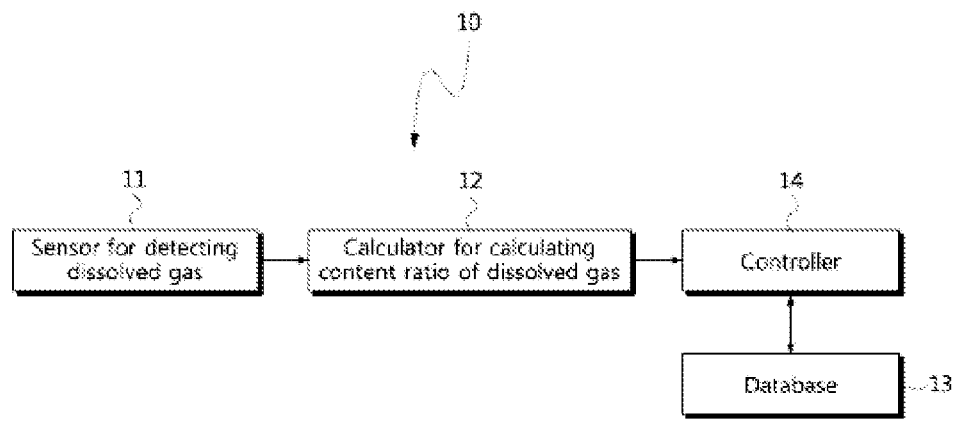
FIG. 1 is a block diagram illustrating a configuration of an apparatus for diagnosing an internal fault of an oil-immersed transformer to which the present application is applied.

FIG. 1 is a block diagram illustrating a configuration of an apparatus for diagnosing an internal fault of an oil-immersed transformer to which the present application is applied.

Referring to FIG. 1, the apparatus of diagnosing the internal fault of the oil-immersed transformer 10 includes a sensor 11 for detecting dissolved gases, a calculator 12 for calculating content ratios of the dissolved gases, a database (DB) 13, and a controller 14.

The sensor 11 for detecting the dissolved gases detects the dissolved gases contained in insulating oil in the oil-immersed transformer. The sensor 11 for detecting the dissolved gases includes an extractor for extracting the dissolved gases from the insulating oil of the oil-immersed transformer, and a detector for determining a magnitude of the dissolved gases extracted from the insulating oil. In the embodiment, the sensor 11 for detecting the dissolved gas extracts hydrogen H2, methane CH4, acetylene C2H2, ethylene C2H4, and ethane C2H6 from the plurality of dissolved gases, and measures quantity of each gas. Among these five dissolved gases, CH4 and C2H6 are classified as a low temperature fault, C2H4 is classified as a high temperature fault, H2 is classified as a low energy discharge, and C2H2 is classified as a high energy discharge.

The calculator 12 for calculating content ratios of the dissolved gases selects four dissolved gases, which are classified according to each of the internal faults, from the five dissolved gases detected by the dissolved gas detecting sensor 11, and calculates a content ratio (%) of each of the four dissolved gases selected and dissolved gases in a total content. Hereinafter, a case that the four dissolved gases of H2, CH4, C2H2, and C2H4 are selected from the five dissolved gases will be described for convenience of description. However, the present invention is not limited thereto, and another grouping of four dissolved gases may be selected. In this embodiment, content ratios of each of the four selected and dissolved gases among the total content of the four selected and dissolved gases, i.e., values of % H2, % CH4, % C2H2, and % C2H4, are calculated. Here, the content ratios of each of the dissolved gases are indicated by percentage when the total content of the dissolved gases consisting of four components is defined as 100%. Accordingly, the content ratio of each of the dissolved gases is calculated by Equation 1 below.

$$\% \ H_2 = \frac{H_2}{H_2 + CH_4 + C_2H_2 + C_2H_4} \times 100$$

$$\% \ CH_4 = \frac{CH_4}{H_2 + CH_4 + C_2H_2 + C_2H_4} \times 100$$

$$\% \ C_2H_2 = \frac{C_2H_2}{H_2 + CH_4 + C_2H_2 + C_2H_4} \times 100$$

$$\% \ C_2H_4 = \frac{C_2H_4}{H_2 + CH_4 + C_2H_2 + C_2H_4} \times 100$$

Equation 1

Of course, in a case that four other dissolved gases are selected from the five dissolved gases, the content ratio of each of the dissolved gases in the total content of the four selected dissolved gases are calculated above.

The database (DB) 13 stores data, which is reference information for determining the internal fault of the immersed transformer. Particularly, in the first embodiment of the present invention, the database DB 13 stores a first xy plane view, including an x-axis and a y-axis on which % H2 and % CH4 are indicated; a second xy plane view, including an x-axis and a y-axis on which % H2 and % C2H2 are indicated; a third xy-plane view, including an x-axis and a y-axis on which % C2H4 and % CH4 are indicated; a fourth xy-plane view, including an x-axis and a y-axis on which % C2H4 and % C2H2 are indicated; and various data related to these plane views. For example, a fault region is classified according to a type of the internal fault. At this time, the four plane views is used to determine the type of the internal fault by using the values of % H2, % CH4, % C2H4, and % C2H4 detected from the oil-immersed transformer 10, of which the internal fault is able to be determined. In the four plane views, after % H2, % CH4, % C2H2 and % C2H4 are detected from each of plural oil-immersed transformers of which the types of the internal faults are known, values of % H2-% CH4, values of % H2-% C2H2, values of % C2H4-% C2H2, and values of % C2H4-% CH4 are preset as x and y coordinates on the first to fourth xy-planes, and a region corresponding to each of the types of the internal faults is distinguished by using each of the x and y coordinates.

Further, in the second embodiment of the present invention, the database 13 stores a two-dimensional plane view determined by values of % H2, % CH4, % C2H4, % C2H2, and various other data related to the two-dimensional plane view. For example, a fault region is distinguished depending on each of the types of the internal faults according to the values of % H2, % CH4, % C2H4, and % C2H2. The two-dimensional plane view is used to determine the type of the internal fault by using the values of % H2, % CH4, % C2H4, and % C2H2 detected from the oil-immersed transformer of which the internal fault is able to be determined. In the two-dimensional plane view, the values of % H2, % CH4, % C2H4 and % C2H2, which are calculated for each of the plural oil-immersed transformer of which the type of the internal fault is known, become four axes, which form the two-dimensional plane view having a square shape. Further, in the two-dimensional plane view, a region is distinguished to correspond to each of the types of the internal faults.

The controller 14 determines the internal fault of the corresponding oil-immersed transformer 10 for the diagnosis by using one or more values selected from the value of % H2 and % CH4, the value of % H2 and % C2H2, the value of % C2H4 and % C2H2, and the value of % C2H4 and % CH4 which are calculated for the oil-immersed transformer for the diagnosis, of which the internal fault is able to be determined, in the first embodiment. Particularly, the controller 14 defines the value of % H2-% CH4, the value of % H2-% C2H2, the value of % C2H4-% C2H2, and the value of % C2H4-% CH4, which are the contents of the dissolved gases detected from the oil-immersed transformer 10 for the diagnosis, as the x and y coordinate respectively. It then, determines the fault region in the first to fourth xy-planes stored in the database (DB) 13, to which each x and y coordinate corresponds. Finally, the controller 14 determines the corresponding internal fault. Further, the controller 14 determines the internal fault of the oil-immersed transformer for the diagnosis by using the values of % H2, % CH4, % C2H4 and % C2H2 calculated for the oil-immersed transformer for the diagnosis, of which the internal fault is determined in the second embodiment. Particularly, the controller 14 determines a fault region in the two-dimensional plane view stored in the database (DB) 13 to which the values of the content ratios of % H2, %

CH4, % C2H4, and % C2H2 of the dissolved gases detected in the oil-immersed transformer for the diagnosis correspond. It then, finally determines the corresponding internal fault.

Here, the oil-immersed transformer of which the internal fault is known refers to the oil-immersed transformer, which has a failure (internal fault), among the oil-immersed transformers used in a field, and it is used for inspecting a correlation between the content ratio by matching the content ratios of the dissolved gases corresponding to the internal fault in the state that the internal fault occurs. On the other hand, the oil-immersed transformer for the diagnosis refers to an oil-immersed transformer of which an internal fault is diagnosed by using the xy-plane view.

FIGS. 2 to 5 are the first to fourth plane views according to the first embodiment of the present invention.

FIGS. 2 to 5 show the first to fourth xy-plane views on which the internal faults according to the content ratios of the corresponding dissolved gases are indicated by defining each of % H2 and % CH4, % H2 and % C2H2, % C2H4 and % C2H2, and % C2H4 and % CH4 as an X axis and a Y axis, respectively, with relation to a plurality of oil-immersed transformers of which the type of the internal fault is already known according to the first embodiment of the present invention. In the embodiment, for example, the content ratio of each dissolved gas during a failure (the type of the internal fault) is analyzed with respect to the plurality of oil-immersed transformers of which the internal faults occur in an operation of the oil-immersed transformers in a field.

Figure 2:
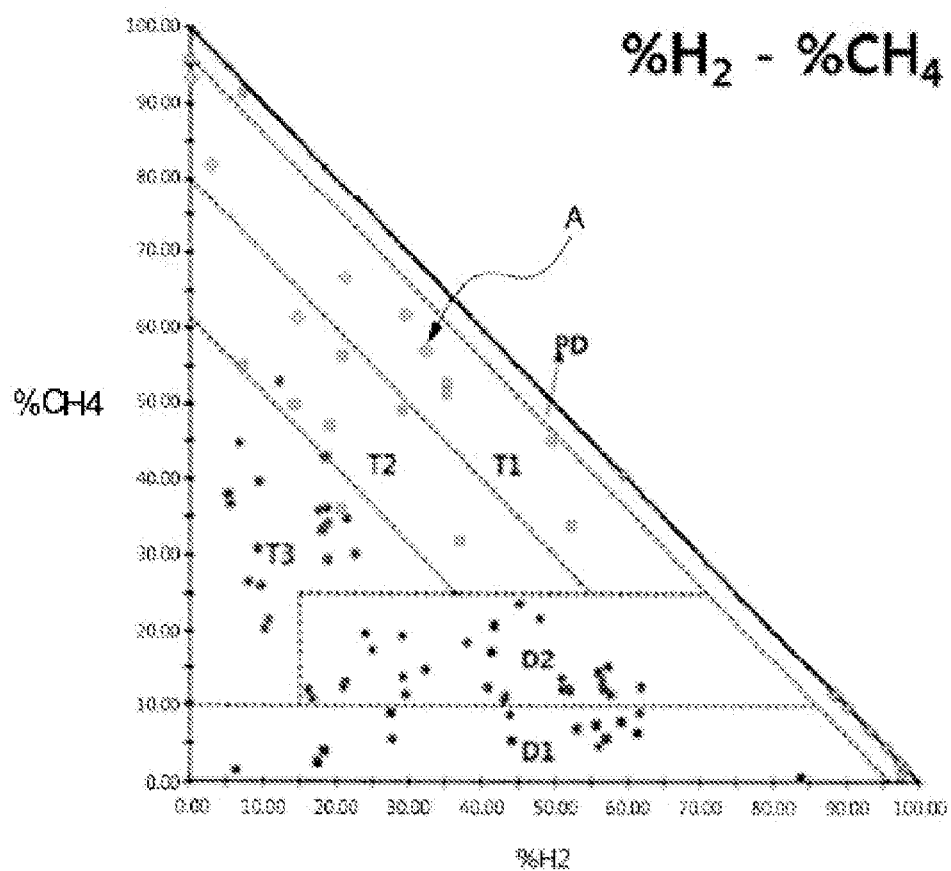
FIGS. 2 to 5 are first to fourth X-Y plane views according to a first embodiment of the present invention.

Particularly, in FIG. 2, % H2 and % CH4 are defined as the x-axis and the y-axis, and a range thereof is set to 0-100%. For example, a reference sign A denotes a specific oil-immersed transformer in which % H2 is 33% and % CH4 is 56%. As described above, % H2-% CH4 of each of ninety three oil-immersed transformers is shown in the first xy-plane view of FIG. 2. Further, the values indicated on the first xy-plane view of FIG. 2 are classified according to each of the types of the internal faults so as to determine a fault region. At this time, the type of the internal fault includes a partial discharge PD, a low energy discharge D1, a high energy discharge D2, a first thermal fault (t<300° C.) T1, a second thermal fault (300° C.<t<700° C.) T2, and a third thermal fault (t>700° C.) T3.

Figure 3:
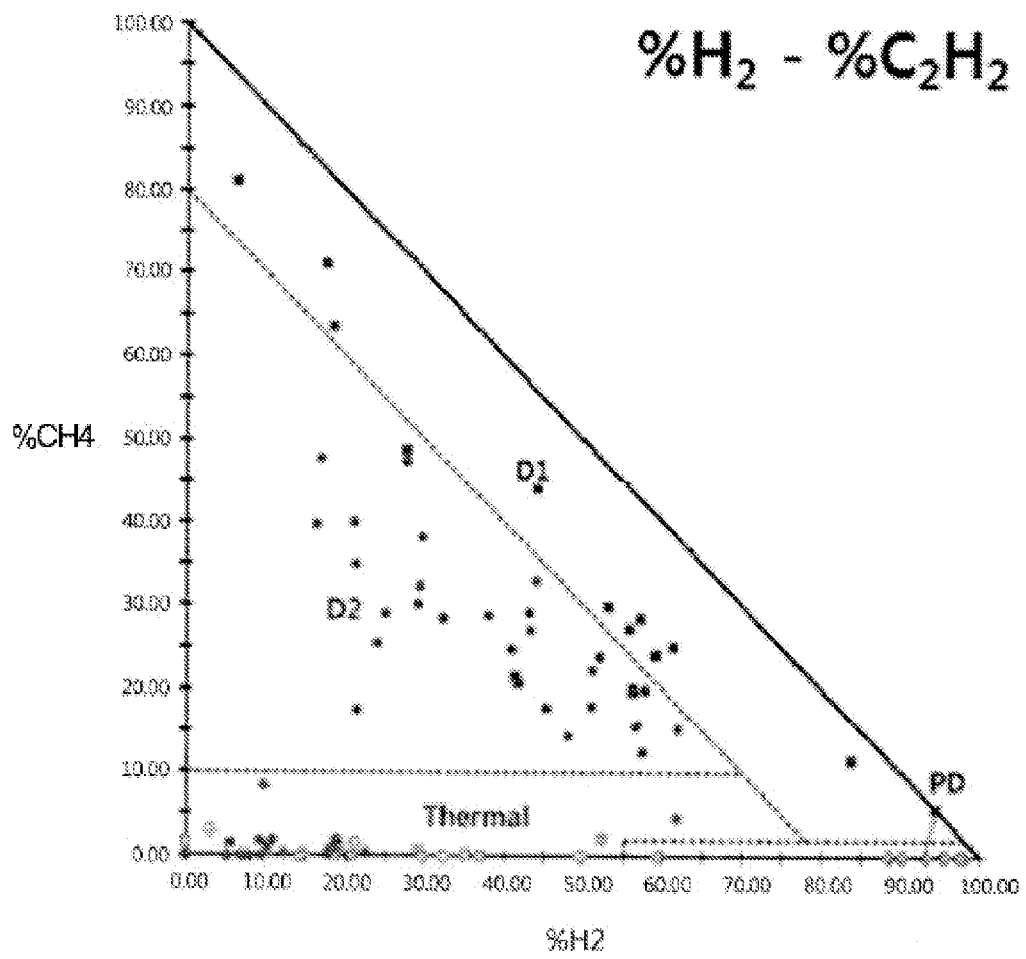
Figure 4:
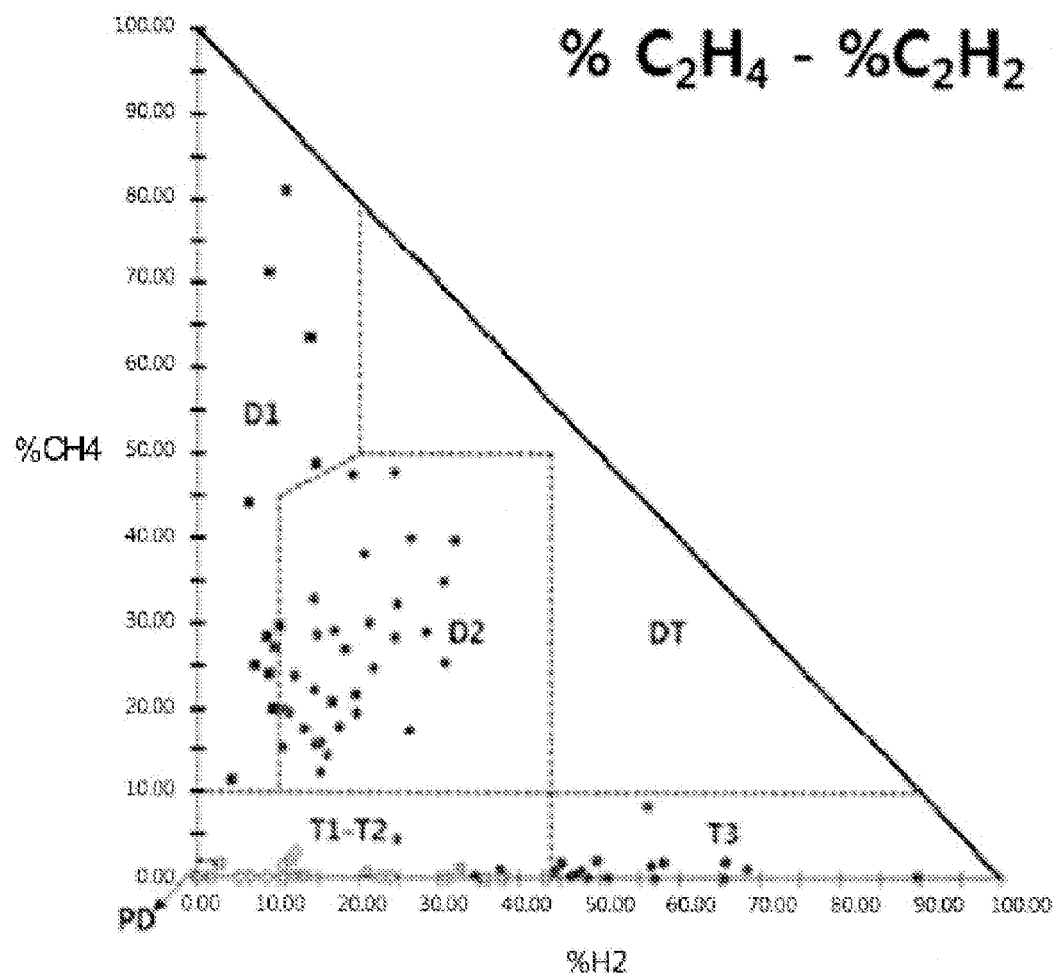
Figure 5:
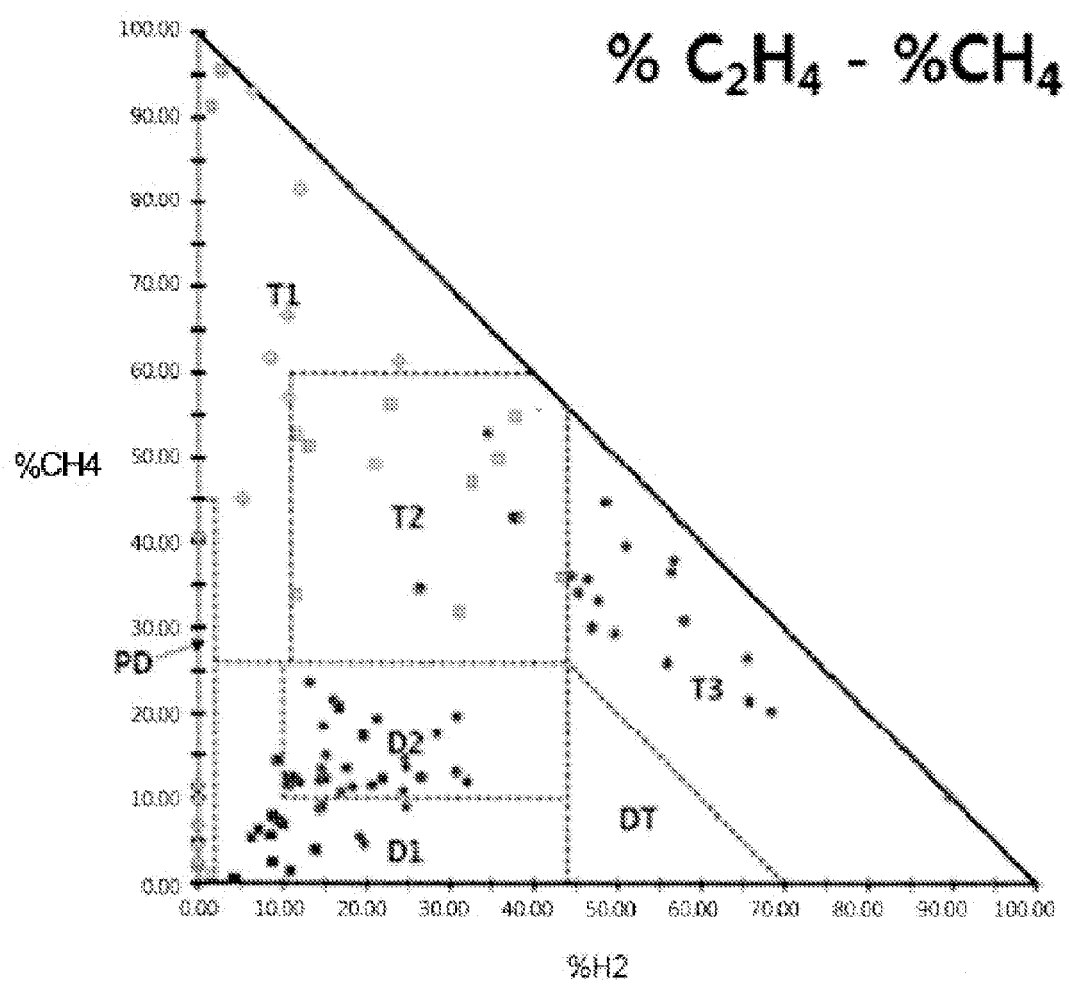

Similarly to FIG. 2, in FIG. 3, % H2 and % C2H2 are set on an x-axis and a y-axis respectively, and the range thereof is set to 0~100%; in FIG. 4, % C2H4 and % C2H2 are set on an x-axis and a y-axis respectively, and the range thereof is set to 0~100%; and in FIG. 5, % C2H4 and % CH4 are set on an x-axis and a y-axis, and the range thereof is set to 0~100%. Further, in FIGS. 3 to 5, the type of the internal faults is classified by using the values indicated on the xy-plane views of FIGS. 2 to 4, so as to determine a fault region.

Firstly, on the second xy-plane view of FIG. 3, the partial discharge PD, a low energy discharge D1, and a high energy discharge D2 are determined in the thermal fault T and the electrical fault E.

Further, on the third xy-plane view of FIG. 4, the first, second, third thermal faults T1, T2 and T3 of the thermal fault T, the partial discharge PD, the low energy discharge D1, the high energy discharge D2 of the electrical fault E, a common region of the thermal fault T, and the electrical fault E are determined.

Further, on the fourth xy-plane view of FIG. 5, the first thermal fault T1, the second thermal fault T2, the third thermal fault T3, the partial discharge PD, the low energy discharge D1, and the high energy discharge D2 are determined.

As shown in FIGS. 2 to 5, on the x- and y-axes of the first to fourth xy-plane views, the value of % H2-% CH4, the value of % H2-% C2H2, the value of % C2H4-% C2H2, and the value of % C2H4-% CH4 are in a range of 0~100%, respectively. Each fault region is located within a triangle shape formed by connecting in a straight line points at which the values are 100% on the x- and y-axes of xy-plane views.

Figure 6:
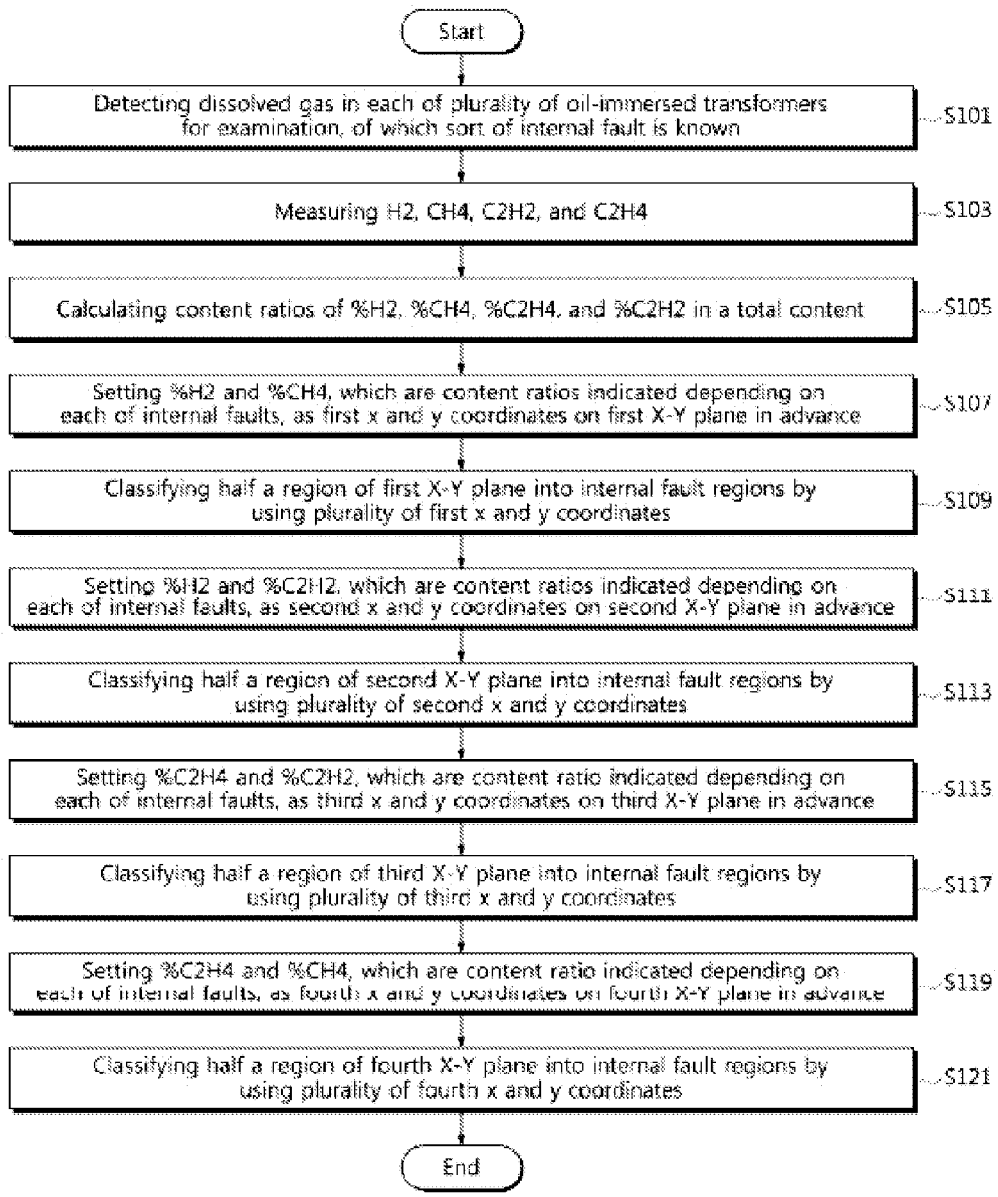
FIG. 6 is a flowchart illustrating a process of constructing the first to fourth X-Y plane views according to the first embodiment of the present invention.

FIG. 6 is a flowchart illustrating a process of setting the first to fourth xy-plane views according to the first embodiment of the present invention.

Referring to FIG. 6, according to the first embodiment of the present invention, the dissolved gases contained in the insulating oil in each of a plurality of oil-immersed transformer of which the internal fault is already known the type of the internal fault are detected in step S101. H2, CH4, C2H2 and C2H4 are extracted from the dissolved gases, which are detected as described above, and the quantities thereof are measured in step S103. The total content of the dissolved gases having the four extracted components is calculated, and each value of content ratios % H2, % CH4, % C2H4 and % C2H2 in the dissolved gases are calculated in step S105. Then, the first to fourth xy-plane views are set respectively by using the values of % H2, % CH4, % C2H4 and % C2H2 calculated as described above.

First, the process of setting the first xy-plane view will be described. The values of % H2 and % CH4, which are the content ratios indicated depending on the types of the internal faults respectively in each oil-immersed transformer of which the types of the internal faults are already known, are set as before first x and y coordinates on the first xy-plane in step S107. Half a region of the first xy-plane is defined as an internal fault region by using the first x and y coordinates in step S109.

Next, the values of % H2 and % C2H2, which are the content ratios indicated depending on the type of the internal faults, are set before as the second x and y coordinates on the second xy-plane in step S111. Half a region of the second xy-plane is defined as the internal fault region by using the second x and y coordinates in step S113.

Further, the values of % C2H4 and % C2H2, which are the content ratios indicated depending on each of the internal faults, are set before as the third x and y coordinates on the third X-Y plane in step S115. Half a region of the third xy-plane is defined as the internal fault region by using the third x and y coordinates in step S117.

Finally, the values of % C2H4 and % CH4, which are the content ratios indicated depending on each of the internal faults, are set in advance as the fourth x and y coordinates on the fourth xy-plane in step S119. Half a region of the fourth xy-plane is defined as the internal fault region by using the fourth x and y coordinates in step S121.

As described above, the first to fourth plane views are used to acquire the content ratio of each of the four dissolved gases extracted from the plurality of the oil-immersed transformers of which the internal faults are previously known. Then, the two content ratios of two dissolved gases selected from the four dissolved gases are set as x and y coordinates on the xy-plane so as to distinguish each fault region. The first to fourth plane views are used to determine the internal fault of the oil-immersed transformer for the diagnosis, of which the internal fault is able to be diagnosed.

Figure 7:
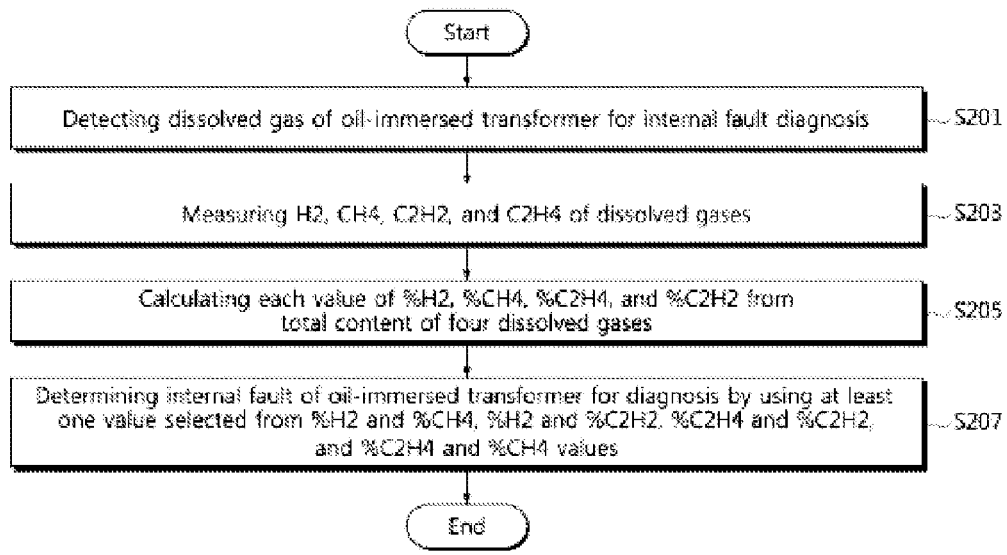
FIG. 7 is a flowchart illustrating a process of diagnosing the internal fault of an oil-immersed transformer through a content ratio of dissolved gases according to the first embodiment of the present invention.

FIG. 7 is a flowchart illustrating a process of diagnosing the internal fault of an oil-immersed transformer through content ratios of dissolved gases according to the first embodiment of the present invention.

Referring to FIG. 7, in the method of diagnosing the internal fault of the oil-immersed transformer according to the first embodiment of the present invention, the dissolved gases are detected from the oil-immersed transformer 10 for the diagnosis, of which the internal fault is able to be diagnosed in step S201. H2, CH4, C2H2, C2H4, and C2H6 are extracted from the dissolved gases, which are detected as described above, and the quantities thereof are measured respectively in step S203. The four dissolved gases classified depending on each of the internal faults are selected from the dissolved gases of the five extracted components, and a total content of the four selected dissolved gases is calculated. Further, the content ratios of each dissolved gas are calculated. That is, in an example of the present invention, the values of % H2, % CH4, % C2H4, and % C2H2 are calculated respectively in step S205. However, the present invention is not limited thereto, but a combination of four of the other dissolved gases may be selected. Then, the internal fault of the oil-immersed transformer 10 for the diagnosis is determined by using at least one value selected from the values of % H2 and % CH4, % H2 and % C2H2, % C2H4 and % C2H2, and % C2H4 and % CH4 which are calculated in step S207. Here, in step S207 of determining the internal fault, a region corresponding to a value of % H2 and % CH4 is determined to be a fault region divided in the first xy-plane view, and the type of internal fault is precisely determined by using the determined fault region. Similarly, a region corresponding to the value of % H2 and % C2H2 is determined to be a fault region divided in the second xy-planes, a region corresponding to the value of % C2H4 and % C2H2 is determined to be a fault region divided in the third xy-plane view, and a region corresponding to the value of % C2H4 and % CH4 is determined in a fault region divided in the fourth xy-plane view. At this time, the determination of the internal fault using the first to fourth xy-plane views may be performed in parallel. Accordingly, the internal fault may be determined by using one or more xy-plane views selected from the first to fourth xy-plane views.

As shown in FIGS. 2 to 7, in the first embodiment of the present invention, the internal fault of the corresponding transformer may be preciously diagnosed by using a combination of the content ratios of two dissolved gases among the content ratios of the dissolved gases selected from the five dissolved gases which are generated during the occurrence of the internal fault of the oil-immersed transformed.

Hereinafter, the method of diagnosing the internal fault of the oil-immersed transformer according to the second embodiment of the present invention will be described in detail.

Figure 8:
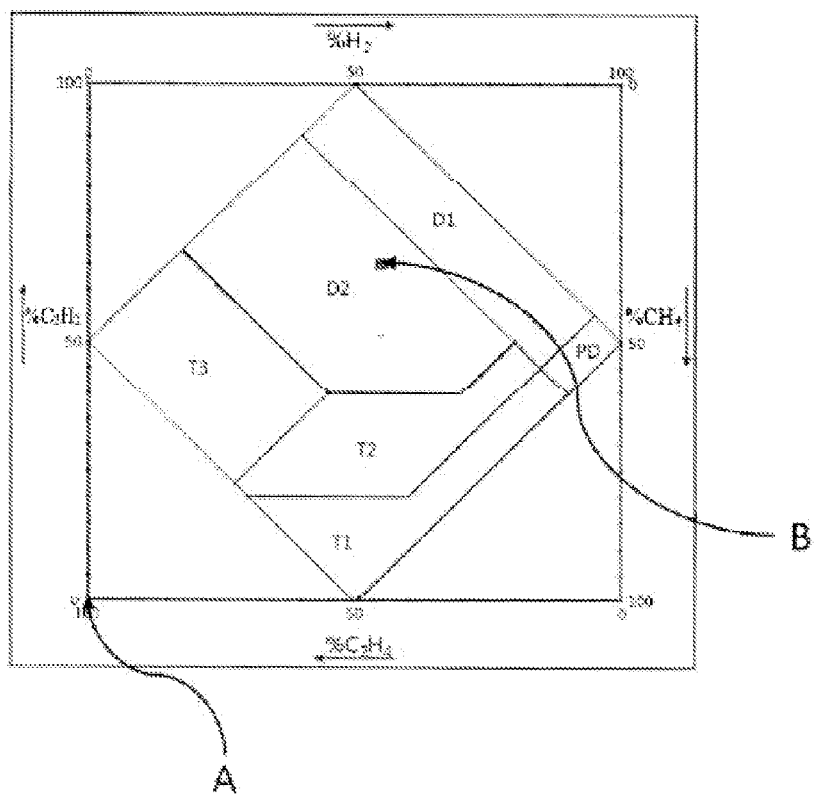
FIG. 8 is a two-dimensional plane view according to a second embodiment of the present invention.

FIG. 8 is a two-dimensional plane view according to a second embodiment of the present invention.

FIG. 8 shows the two dimensional plane view having a square shape which is defined by four axes after % H2, % CH4, % C2H4, and % C2H2 detected for the plurality of the oil-immersed transformers of which the type of the internal faults are known are used as the four axes, according to the second embodiment of the present invention. In the embodiment, for example, the content ratio of each dissolved gas for a failure (the type of the internal fault) is analyzed with respect to the plurality of oil-immersed transformers (of which the type of the internal faults is already known) of which the internal faults occur in an operation of the oil-immersed transformers in a field.

Particularly, in the two dimensional plane with the square shape of FIG. 8, the value of % H2 is used as an upper axis, the value of % CH4 is used as a right axis, the value of % C2H2 is used as a left axis, and the value of % C2H4 is used as a lower axis. On the four axes, the values of % H2, % CH4, % C2H4, and % C2H2 are in a range of 0~100%, respectively. Accordingly, the two-dimensional plane view set as described above has the square shape defined by the four axes. At this time, among the four axes, the % H2 axis and % C2H4 axis are opposite to each other, and the % C2H2 axis and the % CH4 axis are opposite to each other. Further, it is set that one of two values selected from the values of % H2, % CH4, % C2H4, and % C2H2 increases and the other one decreases along two axes from each corner defined by two axes in the square shape. That is, it is set that % CH4 increases and % H2 decreases along each axis from each corner (apex) indicated by a reference sign A.

Further, all fault regions divided within the two-dimensional plane view are located within a diamond shape formed by connecting points, where the values of % H2, % CH4, % C2H4, and % C2H2 become 50% on the four axes, in straight lines. For example, a reference sign B indicates a specific oil-immersed transformer in which % H2 is 30%, % CH4 is 10%, % C2H2 is 20%, and % C2H2 is 40%. Four corners are shown when a vertical line is drawn from the value of the content ratio of the dissolved gas on each axis toward an opposite axis. A center point of a rectangle having the four corners becomes a fault diagnosis point. In the two-dimensional plane view, the fault diagnosis points calculated by the values of the content ratios of the four dissolved gases generated in the oil-immersed transformer for the diagnosis of which the internal fault is able to be diagnosed, are included in the fault region having the diamond shape.

As described above, in the present invention, when the values of % H2, % CH4, % C2H4, and % C2H2 of each of the plurality of oil-immersed transformers of which the type of the internal faults is already known are indicated, the values shown in the two-dimensional plane view of FIG. 8 are classified depending on the types of the internal faults so as to determine the fault region. At this time, the type of the internal faults may be classified into six types, which include a partial discharge PD, a low energy discharge D1, a high energy discharge D2, a first thermal fault (t<300° C.) T1, a second thermal fault (300° C.<t<700° C.) T2, a third thermal fault (t>700° C.) T3.

Figure 9:
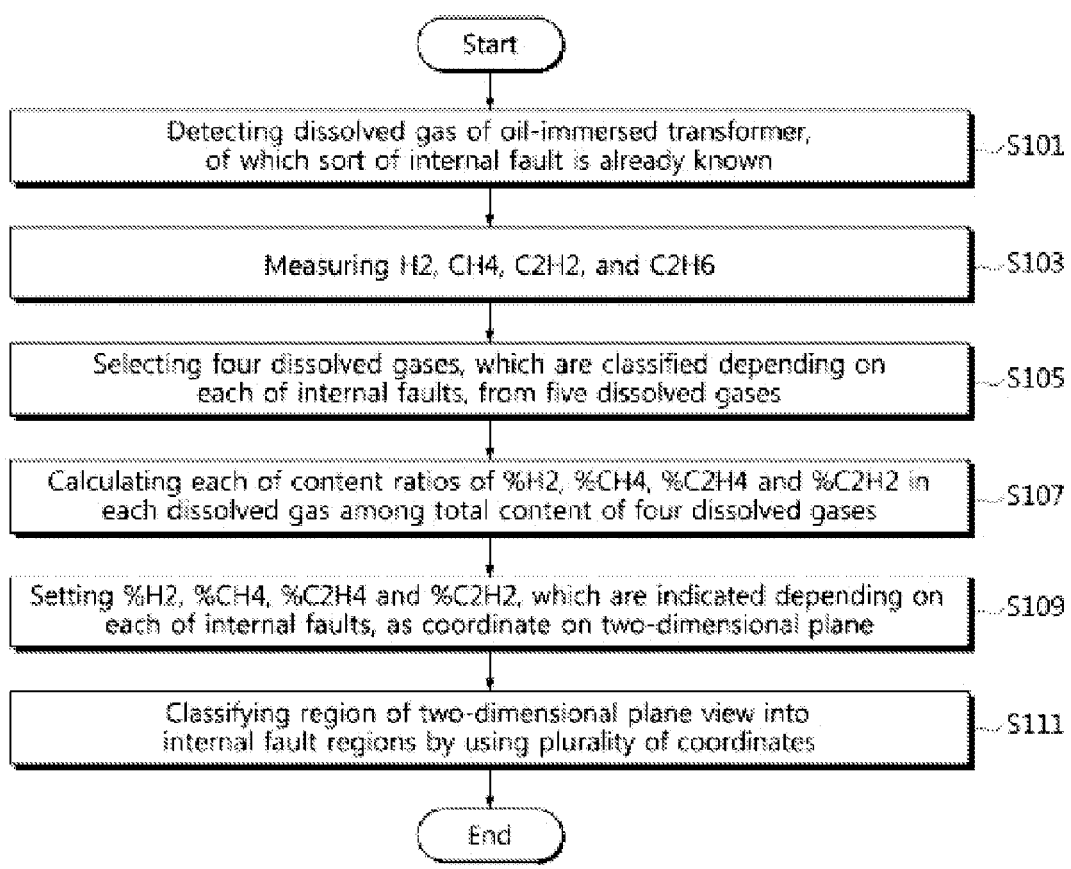
FIG. 9 is a flowchart illustrating a process of constructing a two-dimensional plane view according to the second embodiment.

FIG. 9 is a flowchart illustrating a process of setting the two-dimensional xy-plane view according to the second embodiment.

Referring to FIG. 9, in the second embodiment according to the present invention, the dissolved gases, which are contained in the insulating oil in each of the plurality of oil-immersed transformers of which the internal faults are already known, are detected in step S301. H2, CH4, C2H4, C2H2 and C2H6 are extracted from the dissolved gases, which are detected as described above, and the quantities thereof are measured in step S303. The four dissolved gases classified depending on each of the internal faults are selected from the dissolved gases of the five extracted components in step S305. Then, a total content of the four selected dissolved gases and the content ratio of each dissolved gas to the total content are calculated in step S307. As described above, in an example of the present invention, the values of % H2, % CH4, % C2H4, and % C2H2 are each calculated. Then, the two-dimensional plane view having the square shape is set by using the values of % H2, % CH4, % C2H4 and % C2H2, which were calculated as described. The values of % H2, % CH4, % C2H4 and % C2H2 are indicated as axes on the two-dimensional plane view having the square shape, and the values of % H2, % CH4, % C2H4 and % C2H2, which are the content ratios of each oil immersed transformer of which the type of the internal faults is known, are set in advance as coordinates on the two-dimensional xy-plane in step S309. The region of the two-dimensional plane view having the square shape is divided into internal fault regions by using the plurality of set coordinates in step S311.

As described above, the two-dimensional plane view is used to acquire the content ratio of the four dissolved gases extracted from the plurality of the oil-immersed transformer, of which the type of the internal faults is already known. It then sets, the content ratios as the coordinates on the two dimensional plane view, so as to classify the region of the plane view into the fault regions. The two-dimensional plane view is used to determine the internal fault of the oil-immersed transformer for the diagnosis, of which the internal fault is able to be diagnosed.

Figure 10:
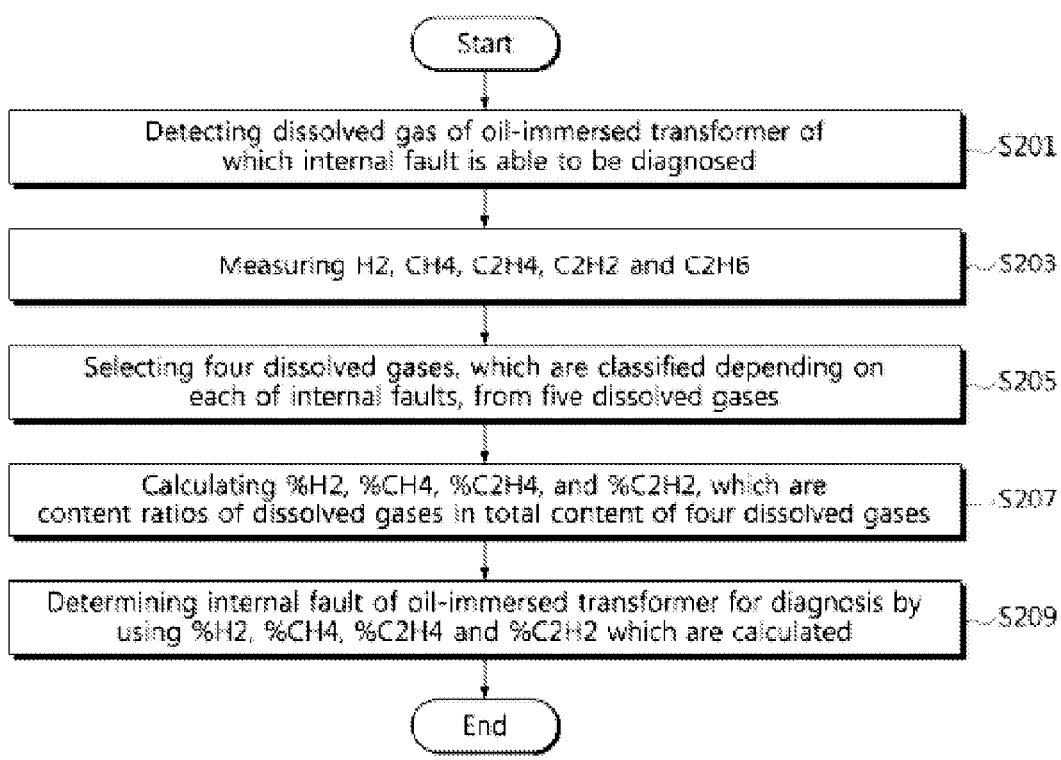
FIG. 10 is a flowchart illustrating a process of diagnosing the internal fault of an oil-immersed transformer through a content ratio of dissolved gases according to the second embodiment of the present invention.

FIG. 10 is a flowchart illustrating a process of diagnosing the internal fault of the oil-immersed transformer through the content ratios of the dissolved gases according to the second embodiment of the present invention.

Referring to FIG. 10, in the process of diagnosing the internal fault of the oil-immersed transformer according to the second embodiment of the present invention, the dissolved gases are detected from the oil-immersed transformer for the diagnosis, of which the internal faults are able to be diagnosed in step S401. H2, CH4, C2H4, C2H2 and C2H6 are extracted from the dissolved gases, which are detected as described above, and the quantities thereof are measured in step S403. The four dissolved gases, which are classified depending on each of the internal faults, are selected from the dissolved gases of the five extracted components in step S405. Then, a total content of the four selected and dissolved gases is calculated, and the content ratio of each dissolved gas to the calculated total content of the four dissolved gases is calculated in step S407. As described above, in the present invention, for convenience of the description, the values of the content ratios of % H2, % CH4, % C2H4, and % C2H2 are calculated. The internal fault of the oil-immersed transformer for the diagnosis is determined by using the calculated values of % H2, % CH4, % C2H4 and % C2H2 in step S409. Here, in step S407 of determining the internal fault, coordinates corresponding to the values of % H2, % CH4, % C2H4, and % C2H4 are determined in a fault region divided on the two-dimensional plane view, and the internal fault is precisely determined by using the determined fault region.

Although the present invention has been described in detail through the exemplary embodiments, it will be known that the present invention is not limited to the contents of the embodiments. It is obvious to those skilled in the art to which the present invention pertains that the present invention may be modified and varied within the scope of the accompanying claims. Even though the variations and modifications are described in the embodiments, and the variation and the modification belong to the technical scope of the present invention. Therefore, the technical scope of the present invention should be defined by the technical spirit of the accompanying claims.

INDUSTRIAL APPLICABILITY

The oil-immersed transformer is electric equipment for increasing or decreasing a supplied voltage, and plays an important role in the electric power supplying system. When the internal fault occurs in the oil-immersed transformer, it may cause a failure in the supply of the electric power. Accordingly, it is important to detect the internal fault, thereby preventing an electrical accident.

In these terms, since the present invention can accurately diagnose the internal fault by extracting and analyzing the dissolved gases contained in the insulating oil in the oil-immersed transformer, the present invention may be efficiently used in the transformer substation, the electric power plant, and the like, to which it is applied, as well as in manufacturing the oil-immersed transformer.

The invention claimed is:

1. A method of diagnosing an internal fault of an oil-immersed transformer through a combination of content ratios of dissolved gases, which is capable of analyzing the dissolved gases contained in the insulation oil of the oil-immersed transformer of which the internal fault is able to be diagnosed, the method comprising:
   a first step of extracting H2, CH4, C2H2, C2H4, and C2H6 from the dissolved gases;
   a second step of selecting four dissolved gases, classified depending on each internal fault, from the five extracted and dissolved gases, so as to calculate a content ratio of each dissolved gas to a total content of the four selected and dissolved gases; and
   a third step of determining a type of the internal fault of the immersed transformer for the diagnosis by enabling one to four combinations, which are selected from combinations of % H2 and % CH4, % H2 and % C2H2, % C2H4 and % C2H2, % C2H4 and % CH4, % H2 and % C2H6, and % C2H4 and % C2H6 which are calculated, to correspond to a predetermined internal fault region.

2. The method as claimed in claim 1, wherein the third step comprises:
   setting values of the content ratio of % H2 and % CH4 of each oil-immersed transformer, of which a type of the internal faults is known, depending on each of a partial discharge PD, a low energy discharge D1, a high energy discharge D2, a first thermal fault (t<300° C.) T1, a second thermal fault (300° C.<t<700° C.), and a third thermal fault (t>700° C.) T3; and
   classifying half a region of the first xy-plane into a partial discharge (PD) fault region, a low energy discharge (D1) fault region, a high energy discharge (D2) fault region, a first thermal fault (t<300° C.) (T1) region, a second thermal fault (300° C.<t<700° C.) (T2) region, and a thermal fault (t>700° C.) region by using the plurality of set coordinates,
   wherein the internal fault of the oil-immersed transformer for the diagnosis is determined by using a region corresponding to x and y coordinates for the values of % H2 and % CH4 calculated in the second step.

3. The method as claimed in claim 2, wherein the values of % H2-% CH4, % H2-% C2H2, % C2H4-% C2H2, and % C2H4-% CH4 are in a range of 0~100% on each x-y axis on the first to fourth xy-plane, and the fault region is located within a triangular shape defined by connecting points, at which the x axis and the y axis are 100%.

4. The method as claimed in claim 3, wherein the content ratio of each dissolved gas, which is calculated in the second step, is included in the fault region within the triangular shape.

5. The method as claimed in claim 1, wherein the third step comprises:
   setting of the values of % H2 and % C2H2, which are content ratios indicated depending on each of a partial discharge (PD), a low energy discharge (D1), and a high energy discharge (D2) of a thermal fault and an electrical fault, as x and y coordinates for each of a plurality of oil-immersed transformers, of which a type of the internal fault is known, on a second xy-plane; and classifying half a region of the second xy-plane into the partial discharge (PD) fault region, a low energy discharge (D1) fault region, and a high energy discharge (D2) fault region of a thermal fault region and an electrical region, wherein the internal fault of the oil-immersed transformer used for diagnosis is determined by using a region corresponding to x and y coordinates for the values of % H2 and % C2H2 calculated in the second step.

6. The method as claimed in claim 5, wherein the values of % H2-% CH4, % H2-% C2H2, % C2H4-% C2H2, and % C2H4-% CH4 are in a range of 0~100% on each x-y axis on the first to fourth xy-plane, and the fault region is located within a triangular shape defined by connecting points, at which the x axis and the y axis are 100%.

7. The method as claimed in claim 1, wherein the third step comprises:

setting values of the content ratio of % C2H4 and % C2H2 of each oil-immersed transformer, of which a type of the internal fault is known, depending on each of a partial discharge PD, a low energy discharge D1, a high energy discharge D2, a first thermal fault (t<300° C.) T1, a second thermal fault (300° C.<t<700° C.) T2, and a third thermal fault (t>700° C.) T3, as x and y coordinates on a third xy-plane; and classifying half a region of the first xy-plane into a partial discharge (PD) fault region, a low energy discharge (D1) fault region, a high energy discharge (D2) fault region, a first thermal fault (t<300° C.) (T1) region, a second thermal fault (300° C.<t<700° C.) (T2) region, and a thermal fault (t>700° C.) region by using the plurality of set coordinates, wherein the internal fault of the oil-immersed transformer for the diagnosis is determined by using a region corresponding to x and y coordinates for the values of % C2H4 and % C2H2 calculated in the second step.

8. The method as claimed in claim 7, wherein the values of % H2-% CH4, % H2-% C2H2, % C2H4-% C2H2, and % C2H4-% CH4 are in a range of 0~100% on each x-y axis on the first to fourth xy-plane, and the fault region is located within a triangular shape defined by connecting points, at which the x axis and the y axis are 100%.

9. The method as claimed in claim 1, wherein the third step comprises:

setting values of the content ratio of % C2H4 and % CH4 of each oil-immersed transformer, of which a type of the internal faults is known, depending on each of a partial discharge PD, a low energy discharge D1, a high energy discharge D2, a first thermal fault (t<300° C.) T1, a second thermal fault (300° C.<t<700° C.) T2, and a third thermal fault (t>700° C.) T3, as x and y coordinates on a four X-Y plane; and classifying half a region of the fourth xy-plane into a partial discharge (PD) fault region, a low energy discharge (D1) fault region, a high energy discharge (D2) fault region, a first thermal fault (t<300° C.) (T1) region, a second thermal fault (300° C.<t<700° C.) (T2) region, and a thermal fault (t>700° C.) (T3) region by using the plurality of set coordinates, wherein the internal fault of the oil-immersed transformer for the diagnosis is determined by using a region corresponding to x and y coordinates for the values of % C2H4 and % CH4 calculated in the second step.

10. The method as claimed in claim 9, wherein the values of % H2-% CH4, % H2-% C2H2, % C2H4-% C2H2, and % C2H4-% CH4 are in a range of 0~100% on each x-y axis on the first to fourth xy-plane, and the fault region is located within a triangular shape defined by connecting points, at which the x axis and the y axis are 100%.

11. A method of diagnosing an internal fault of an oil-immersed transformer through a combination of content ratios of dissolved gases, the method comprising:

a first step of extracting the dissolved gases of H2, CH4, C2H2, C2H4, and C2H6 from each oil-immersed transformer of which a type of the internal faults is known;

a second step of selecting four dissolved gases, classified depending on each internal fault, from the five extracted and dissolved gases, so as to calculate a content ratio of each dissolved gas to a total content of the four selected and dissolved gases;

a third step of classifying half a region of the first xy-plane into the internal fault region by using the plurality of the first x and y coordinates after setting the values of % H2 and % CH4, which are content ratios indicated by each internal fault, as the first x and y coordinates respectively on the first xy-plane;

a fourth step of classifying half a region of the second xy-plane into the internal fault region by using the plurality of the second x and y coordinates after setting the values of % H2 and % C2H2, which are content ratios indicated by each internal fault, as the second x and y coordinates respectively on the second xy-plane;

a fifth step of classifying half a region of the third xy-plane into the internal fault region by using the plurality of the third x and y coordinates after setting the values of % C2H4 and % C2H2, which are content ratios indicated by each internal fault, as the third x and y coordinates respectively on the third xy-plane;

a sixth step of classifying half a region of the fourth xy-plane into the internal fault region by using the plurality of the fourth x and y coordinates after setting the values of % C2H4 and % CH4, which are content ratios indicated by each internal fault, as the fourth x and y coordinates respectively on the fourth xy-plane;

a seventh step of calculating the values of % H2, % CH4, % C2H2, and % C2H4, which are content ratios of four dissolved gases extracted from the oil-immersed transformer for the diagnosis after extracting the dissolved gases of H2, CH4, C2H2, and C2H4 from the insulating oil of the oil-immersed transformer for the diagnosis, of which the internal fault is diagnosed; and an eighth step of determining the internal fault of the oil-immersed transformer for the diagnosis by using one or more values selected from the values of % H2 and % CH4, the values of % H2 and % C2H2, the values of % C2H4 and % C2H2, and the values of % C2H4 and % CH4 among the content ratios of the dissolved gases calculated in the seventh step.

12. A method of diagnosing an internal fault of an oil-immersed transformer through content ratios of dissolved gases, which is capable of analyzing dissolved gases contained in insulation oil of the oil-immersed transformer of which the internal fault is able to be diagnosed, the method comprising:

a first step of extracting H2, CH4, C2H4, C2H2, and C2H6 from the dissolved gases;

a second step of selecting four dissolved gases, classified depending on each internal fault, from the five extracted and dissolved gases, so as to calculate a content ratio of each dissolved gas to a total content of the four selected dissolved gases; and a third step of determining the internal fault of the oil-immersed gases for the diagnosis in correspondence to the content ratios of the four dissolved gases which are calculated and an internal fault region according to the content ratios of the four dissolved gases which are predetermined.

13. The method as claimed in claim 12, wherein the second step comprises:

setting values of the content ratio of % H2, % CH4, % C2H4, and % C2H2 of the dissolved gases of each oil-immersed transformer, of which a type of the internal faults is known, indicated depending on each of a partial discharge PD, a low energy discharge D1, a high energy discharge D2, a first thermal fault (t<300° C.) T1, a second thermal fault (300° C.<t<700° C.), and a third thermal fault (t>700° C.) T3 on a two-dimensional plane in advance; and classifying the two-dimensional plane into six fault regions corresponding to each fault by using the set content ratios, wherein a region corresponding to the four content ratios calculated in the second step is determined in the fault regions divided on the two-dimensional plane, and the internal fault of the oil-immersed transformer for the diagnosis is determined by using the determined fault region.

14. The method as claimed in claim 13, wherein the two-dimensional plane has a square shape defined by four axes, the values of % H2, % CH4, % C2H4, and % C2H2 are in a range of 0~100% on the four axes respectively, and each of the divided fault regions is located within a diamond shape formed by connecting points, at which the values of % H2, % CH4, % C2H4, and % C2H2 of the four axes are 50% respectively, by straight lines.

15. The method as claimed in claim 14, wherein the four axes are formed so that an axis of % H2 and an axis of % C2H4 are opposite to each other and an axis of % C2H2 and an axis of % CH4 are opposite to each other.

16. The method as claimed in claim 14, wherein in the two-dimensional plane, one of two values selected from the values of % H2, % CH4, % C2H4, and % C2H2 increases along two axes from each corner defined by the two axes, and the other one decreases.

17. The method as claimed in claim 14, wherein the four content ratios calculated in the second step are included in the fault region having the diamond shape.

18. A method of diagnosing an internal fault of an oil-immersed transformer through a composition ratio of dissolved gas, the method comprising:

a first step of extracting the dissolved gases of H2, CH4, C2H2, C2H4, and C2H6 from each oil-immersed transformer of which a type of the internal fault is known;

a second step of selecting four dissolved gases, classified depending on each internal fault, from the five dissolved gases which are extracted from each of a plurality of oil-immersed transformers of which a type of the internal fault is known, so as to calculate a content ratio of each dissolved gas to a total content of the four selected dissolved gases;

a third step of setting values of the content ratios of % H2, % CH4, % C2H4, and % C2H2 of the dissolved gases of each oil-immersed transformer, of which a type of the internal faults is known, indicated depending on each of a partial discharge PD, a low energy discharge D1, a high energy discharge D2, a first thermal fault (t<300° C.) T1, a second thermal fault (300° C.<t<700° C.), and a third thermal fault (t>700° C.) T3 on a two-dimensional plane in advance, so as to classify the two-dimensional plane into the fault region corresponding to each fault by using the values of the content ratios which are set;

a fourth step of extracting the dissolved gases from insulating oil of the oil-immersed transformer which is able to be diagnosed, so as to calculate the values of % H2, % CH4, % C2H4, and % C2H2, which are the content ratios of the dissolved gases to the total content of the extracted dissolved gases; and a fifth step of deciding the values of the content ratios of % H2, % CH4, % C2H4, and % C2H2 of the dissolved gases of each oil-immersed transformer for diagnosis, which are calculated in the fourth step in a fault region of the two-dimensional plane, so as to determine the internal fault of the oil-immersed transformer by using the decided fault region.

\* \* \* \* \*